United States Patent [19]

Bischoff et al.

[11] Patent Number: 5,407,923
[45] Date of Patent: Apr. 18, 1995

[54] SUBSTITUTED DERIVATIVES OF DEOXYMYOINOSITOL, PROCESS FOR THEIR PREPARATION AND THEIR USE IN MEDICAMENTS

[75] Inventors: Erwin Bischoff; Zhan Gao, both of Wuppertal; Stefan Wohlfeil, Hilden; Gabriele Hecker, Wuppertal, all of Germany; Jeannine Cleophax, Palaiseau, France; Didier Dubreuil, Juvisy/Orge, France; Stéphane Gero, Les Ulis, France; Alice Olesker, GIF-sur-Yvette, France; Catherine Verre-Sebrie, Les Ulis, France; Mauro V. de Almeida, GIF-sur-Yvette, France; Georges Vass, GIF-sur-Yvette, France

[73] Assignee: Bayer Pharma, Sens, France
[21] Appl. No.: 106,156
[22] Filed: Aug. 12, 1993

[30] Foreign Application Priority Data

Aug. 18, 1992 [FR] France ................ 92 10109

[51] Int. Cl.$^6$ ........................ A61K 31/66; C07F 9/117
[52] U.S. Cl. .................................... 514/103; 558/161
[58] Field of Search ............... 558/161; 514/103, 104

[56] References Cited

U.S. PATENT DOCUMENTS

4,755,612  7/1988  Vacca et al. ................... 549/220

FOREIGN PATENT DOCUMENTS

0497234  8/1992  European Pat. Off. .

OTHER PUBLICATIONS

Natural Product Reports (1990), 1–23.
Phosphoinositides and Receptor Mechanisms, p. 1–24 (1986), Alan R. Liss, Inc. New York.
Agents and Actions 19 (1986), 80–85.
Br. J. Pharmac., 89 (1986), 803–807.
TIBS 13 (1988), 148.
TIBS 14 (1989), 139.
J. Chem. Soc. Chem. Commun., 1988, pp. 1384–1385.
Pure & Appl. Chem., vol. 62, No. 10, pp. 2031∝2034 (1990).
J. C. Sheehan, S. L. Ledis, J. Am. Chem. Soc. 95, 875 (1973).
F. E. Frerman et al., J. Biol. Chem. 258, 7087–7093 (1982).
N. B. Benoiton, K. Kuroda, Int. Pept. Prot. Res. 17, 197–204 (1981).
BBRC 146 (1987) 1071–1078, A. J. Willcocks, A. M. Cooke, B. V. L. Potter and S. R. Nahorski.
William W. Y. Lo and John Hughs, Neurosience Letters 81 (1987) 331–334.
A. M. Cooke, S. R. Nahorski and B. L. V. Potter, FEBS-Letters 242 (1989) 373–377.
H. M. Korchak, L. E. Rutherford and G. Weissmann, J. B. C., 259 (1984) 4070–4075.
Tetrahedron Letters, vol. 30, No. 27, 1989, pp. 3557–3560.
Bulletin of the Chemical Society of Japan, vol. 45, No. 10, 1972, pp. 3226–3227.

Primary Examiner—Mary C. Lee
Assistant Examiner—Michael G. Ambrose
Attorney, Agent, or Firm—Sprung Horn Kramer & Woods

[57] ABSTRACT

Substituted derivatives of deoxymyoinositol of general formula (I):

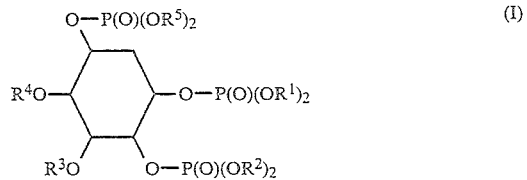

in which
$R^1$, $R^2$ and $R^5$ are identical or different and represent a linear or branched alkyl group of 3 to 14 carbon atoms.
$R^3$ and $R^4$ are identical or different and represent a hydrogen atom, a protecting group of the hydroxyl groups or the residue of formula —CO—(CH$_2$)$_n$—CH$_3$ in which
n represents the number 12, 13, 14, 15, 16 or 17, and their salts, process for preparing them and their use in medicaments.

9 Claims, No Drawings

SUBSTITUTED DERIVATIVES OF DEOXYMYOINOSITOL, PROCESS FOR THEIR PREPARATION AND THEIR USE IN MEDICAMENTS

The present invention relates to new substituted derivatives of deoxymyoinositol, to a process for their preparation and to their use in medicaments, in particular as anti-inflammatories.

It is known that D-myoinositol 1,4,5-triphosphate (IP$_3$) is the second messenger of a large number of receptors. Fastening of an effector molecule to the receptor leads to activation of phospholipase C which, from phosphatidylinositol 4,5-biphosphate, releases diacylglycerol (DAG) and D-myoinositol 1,4,5-triphosphate (IP$_3$). DAG is an activator of the protein kinase C, whereas IP$_3$ causes a temporary rise in cytosolic Ca$^{2+}$ by bonding to an intracellular receptor [see Natural Product Reports, (1990) 1-23; Phophoinositides and Receptor Mechanisms, p. 1-24 (1986); Alan R. Liss. Inc. New York, Ed Putney, I. W. Fr., Agents and Actions, 19 (1986), 80-85; Br. J. Pharmac., 89 (1986), 803-807; TIBS 13 (1988), 148; TIBS (1989), 139].

The present invention relates to compounds of general formula (I):

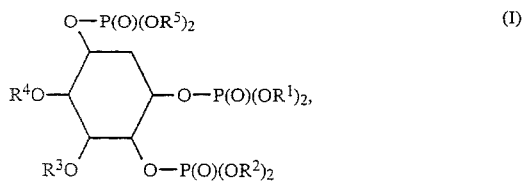

in which

R$^1$, R$^2$ and R$^5$ are identical or different and represent a linear or branched alkyl group of 3 to 14 carbon atoms, R$^3$ and R$^4$ are identical or different and represent a hydrogen atom, a protecting group of the hydroxyl groups or the residue of formula —CO—(CH$_2$)$_n$—CH$_3$ in which n represents the number 12, 13, 14, 15, 16 or 17, and their salts.

In the context of the present invention, the salts are preferred which are faultless from the physiological viewpoint. The salts of the compounds according to the present invention which are faultless from the physiological viewpoint may be salts of the compounds according to the present invention with inorganic acids, carboxylic acids or sulphonic acids. The salts obtained with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid are preferred in particular.

There may also be mentioned the salts obtained with the usual bases, such as, for example, alkali metal salts (for example the sodium or potassium salts), alkaline-earth metal salts (for example the calcium or magnesium salts), or ammonium salts derived from aqueous ammonia or organic amines such as, for example, diethylamine, triethylamine, ethyldiisopropylamine, procaine, N-methylmorpholine, N-methylpiperidine or dihydroabietylamine or tris(hydroxymethyl)aminomethane (Tris).

The compounds according to the invention may exist in the form of stereoisomers which are symmetrical with respect to each other in a mirror (enantiomers) or which are not symmetrical with respect to each other in a mirror (diastereoisomers). The invention relates both to the antipodes and to the racemic forms as well as to the mixtures of diastereoisomers. The racemic forms may be separated, as well as the diastereoisomers, in a known way into the constituents which are homogeneous from the stereoisomeric viewpoint [see E. L. Eliel, Stereochemistry of Carbon Compounds, McGraw Hill, 1962].

Additionally, the substituents e.g the compounds according to the invention may occupy an axial or equatorial position on the cyclohexane skeleton. It is preferable that the substituents occupy positions corresponding to the stereochemistry of 1,4,5-IP$_3$ known in the literature [see J. Chem. Soc., Chem. Commun., 1988, pages 1383-1385 and Pure Appl. Chem., 62 (10), pages 2031-2034, 1990].

In the context of the definition shown above, the protecting group of the hydroxyl groups is generally a protecting group of the following series: trimethylsilyl, triethylsilyl, triisopropylsilyl, tert-butyldimethylsilyl, tert-butyldiphenylsilyl, triphenylsilyl, trimethylsilylethoxycarbonyl, benzyl, triphenylmethyl (trityl), monomethoxytrityl (MMTr), dimethoxytrityl (DMTr), benzyloxycarbonyl, 2-nitrobenzyl, 4-nitrobenzyl, 2-nitrobenzyloxycarbonyl, 4-nitrobenzyloxycarbonyl, tert-butyloxycarbonyl, allyloxycarbonyl, 4-methoxybenzyl, 4-methoxybenzyloxycarbonyl, formyl, acetyl, trichloroacetyl, 2,2,2-trichloroethoxycarbonyl, 2,4-dimethoxybenzyl, 2,4-dimethoxybenzyloxycarbonyl, methoxymethyl, methylthiomethyl, methoxyethoxymethyl, [2-(trimethylsilyl)ethoxy]methyl, 2-(methylthiomethoxy)ethoxycarbonyl, tetrahydropyranyl, benzoyl, 4-methylbenzoyl, 4-nitrobenzoyl, 4-fluorobenzoyl, 4-chlorobenzoyl or 4-methoxybenzoyl.

The compounds of general formula (I) in which:

R$^1$, R$^2$ and R$^5$ are identical or different and represent a linear or branched alkyl group of 4 to 8 carbon atoms, R$^3$ and R$^4$ are identical or different and represent a hydrogen atom, a benzyl group or the residue of formula —CO—(CH$_2$)$_n$—CH$_3$ in which n represents the number 12, 13, 14, 15 or 16, and their salts, are preferred.

In particular, the compounds of general formula (I) in which

R$^1$, R$^2$ and R$^5$ are identical or different and represent a linear or branched alkyl group of 4 carbon atoms, R$^3$ and R$^4$ are identical or different and represent a hydrogen atom or the residue of formula —CO—(CH$_2$)$_n$—CH$_3$ in which n represents the number 12, 13, 14 or 15, and their salts, are preferred.

The compounds of general formula (I) in which

R$^1$, R$^2$ and R$^5$ represent the n-butyl group, and

R$^3$ and R$^4$ are identical or different and represent a hydroxyl group or the residue of formula —CO—(CH$_2$)$_n$—CH$_3$ in which n represents the number 12 or 14, and their salts, are very particularly preferred.

Additionally, there is proposed according to the invention a process for the preparation of the compounds of general formula (I) and of their salts, which is characterised in that compounds of general formula (II):

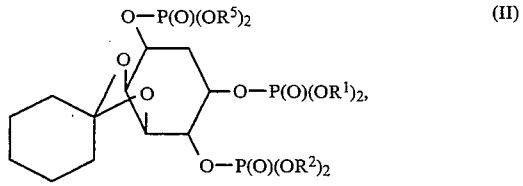

in which

R¹, R² and R⁵ have the meaning shown above, are catalytically hydrogenated in inert solvents, optionally in the presence of a base, with release of the hydroxyl functional groups, and then, when R³ and/or R⁴ do not represent a hydrogen atom, acylation is carried out with compounds of general formula (III):

in which n has the meaning given above and

X represents a hydroxyl group or a typical leaving group such as tosylate, mesylate, chlorine, bromine or iodine, preferably chlorine or iodine, in inert solvents, optionally in the presence of a base and/or of an additional reactant.

The process according to the invention may be illustrated by way of example by the following reaction scheme:

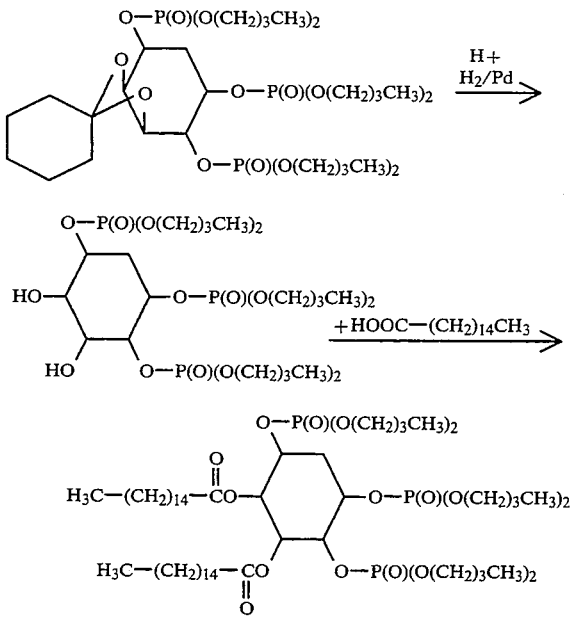

The inert organic solvents which remain unchanged under the conditions of the reaction are suitable as solvents for the process. Halogenated hydrocarbons, such as dichloromethane, trichloromethane, tetrachloromethane, 1,2-dichloroethane, trichloroethane, tetrachloroethane and trichloroethylene, hydrocarbons such as benzene, xylene, toluene, hexane, cyclohexane or petroleum fractions, nitromethane, dimethylformamide, acetonitrile or phosphoric acid hexamethyltriamide are found among these solvents. It is also possible to use mixtures of these solvents. Dichloromethane and acetonitrile are particularly preferred.

The standard basic compounds are suitable as bases for the process. These compounds are preferably alkali metal and alkaline-earth metal hydroxides such as lithium hydroxide, sodium hydroxide, potassium hydroxide or barium hydroxide, alkali metal hydrides such as sodium hydride, alkali metal or alkaline-earth metal carbonates such as sodium carbonate or potassium carbonate, or alkali metal alkoxides such as, for example, sodium methoxide or sodium ethoxide, potassium methoxide or potassium ethoxide or potassium tert-butoxide, or organic amines such as benzyltrimethylammonium hydroxide, tetrabutylammonium hydroxide, pyridine, dimethylaminopyridine, triethylamine, N-methylpiperidine, 1H-tetrazole or tris(hydroxymethyl)aminomethane. 1H-Tetrazole and tris(hydroxymethyl)aminomethane are preferred.

The base is used in a quantity from 1 to 3 mol, preferably from 1 to 1.5 mol, per mole of compound of general formula (II).

Generally, the process is implemented in a temperature range from 0° C. to 150° C., preferably from 25° to 40° C.

Generally, the process is implemented at normal pressure. However, it is possible to implement the process at reduced pressure or under pressure (for example, in a pressure range from $0.5 \times 10^5$ Pa to $5 \times 10^5$ Pa (0.5 to 5 bar)).

Hydrogenolysis intended to cleave the protecting groups, in particular benzyl-type protecting groups, is carried out with hydrogen in inert solvents such as alcohols, ethers or halogenated hydrocarbons or mixtures thereof, with catalysts such as Raney nickel, palladium, palladium-on-animal-charcoal or platinum. Palladium-on-animal-charcoal is preferred [see Th. Greene: "Protective Groups in Organic: Synthesis", J. Wiley & Sons, 1981, New York].

The catalyst is used in a quantity from 0.1 to 1 mol, preferably from 0.2 to 0.3 mol, per mole of compound of general formula (II).

Generally, hydrogenolysis is carried out in a temperature range from 0° to 150° C., preferably from 25° to 40° C.

Generally, hydrogenolysis takes place at normal pressure. However, it is also possible to implement the process at reduced pressure or under pressure (for example, in a pressure range from $0.5 \times 10^5$ Pa to $5 \times 10^5$ Pa (0.5 to 5 bar)).

Acylation likewise takes place in one of the solvents mentioned above, preferably in acetonitrile or in dichloromethane.

The bases mentioned above are also suitable for the acylation and dimethylaminopyridine is preferred among them.

Acylation generally takes place in a temperature range from 0° to 130° C. preferably at room temperature Acylation generally takes place at normal pressure. However, it is possible to implement the process at reduced pressure or under pressure (for example, in a pressure range from $0.5 \times 10^5$ Pa to $5 \times 10^5$ Pa (0.5 to 5 bar)).

In general, dehydrating agents, such as those which are known in peptide chemistry, are used as an additional reactant.

There may be used, as dehydrating reactants, carbodiimides such as, for example, diisopropylcarbodiimide, dicyclohexylcarbodiimide or N-(3-dimethylaminopropyl)-N'-ethylcarbodiimide hydrochloride, or carbonyl compounds such as carbonyldiimidazole, or 1,2-oxazolium compounds such as 2-ethyl-5-phenyl-1,2-oxazolium-3'-sulphonate, propanephosphonic acid anhydride, isobutyl chloroformate, benzotriazolyloxy-tris(dimethylamino)-phosphonium hexafluorophosphate, phosphoric acid diphenylester azide or methanesulphonic acid chloride, optionally in the presence of bases such as triethylamine, N-ethylmorpholine, N-methylpiperidine, dicyclohexylcarbodiimide and N-hydroxysuccinimide (see J. C. Sheehan, S. L. Ledis, J. Am. Chem. Soc., 95, 875 (1973); F. E. Frerman et al., J. Biol. Chem., 225, 507 (1982) and N. B. Benoton, K. Kluroda, Int. Pept. Prot. Res., 13, 403 (1979), 17, 187 (1981)].

The compounds of general formula (III) are known or may be prepared by the usual processes.

The compounds of general formula (II) are known and may be prepared by reacting compounds of general formula (IV):

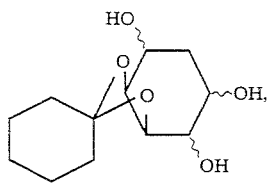

(IV)

with compounds of general formula (V):

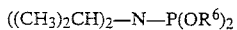

((CH$_3$)$_2$CH)$_2$—N—P(OR$^6$)$_2$ (V), in which

R$^6$ has the same meaning as that shown above for the substituents R$^1$, R$^2$ and R$^5$, in inert solvents, optionally in the presence of a base and then an oxidising agent.

The solvents which may be used for the process are the inert organic solvents which are not subjected to modification under the conditions of the reaction. Halogenated hydrocarbons such as dichloromethane, trichloromethane, tetrachloromethane, 1,2-dichloroethane, trichloroethane, tetrachloroethane or trichloroethylene, hydrocarbons such as benzene, xylene, toluene, hexane, cyclohexane or petroleum fractions, nitromethane, dimethylformamide, acetonitrile or phosphoric acid hexamethyltriamide are found among the latter. It is also possible to use mixtures of these solvents. Dichloromethane and acetonitrile are particularly preferred.

The bases which may be used for the process are the standard basic compounds. These are preferably alkali metal or alkaline-earth metal hydroxides such as lithium hydroxide, sodium hydroxide, potassium hydroxide or barium hydroxide, alkali metal hydrides such as sodium hydride, alkali metal carbonates or alkaline-earth metal carbonates such as sodium carbonate or potassium carbonate, or alkali metal alkoxides such as, for example, sodium methoxide or sodium ethoxide, potassium methoxide or potassium ethoxide or potassium tert-butoxide, or organic amines such as benzyltrimethylammonium hydroxide, tetrabutylammonium hydroxide, pyridine, dimethylaminopyridine, triethylamine, N-methylpiperidine, 1H-tetrazole or tris(hydroxymethyl)aminoethane. 1H-Tetrazole and tris(hydroxymethyl)aminomethane are preferred.

The base is used in a quantity from 1 to 3 mol, preferably from 1 to 1.5 mol, per mole of hydroxyl of the compound of general formula (IV).

The oxidising agents which are suitable are, for example, tert-butyl hydroperoxide, m-chloroperbenzoic acid or iodopyridine. tert-Butyl hydroperoxide is preferred.

In general, the process is implemented in a temperature range from 0° to 150° C., preferably from 25° to 40° C.

The process generally takes place at normal pressure. However, it is also possible to implement the process at reduced pressure or under pressure (for example, in a range from $0.5 \times 10^5$ Pa to $5 \times 10^5$ Pa (0.5 to 5 bar)).

The compounds of general formula (IV) are largely novel and may be prepared by reacting compounds of general formula (VI):

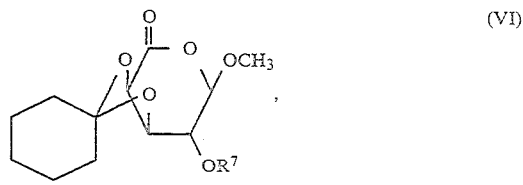

(VI)

in which

R$^7$ represents a typical protecting group of the hydroxyl groups, preferably the benzyl group, first of all with mercuric chloride and thiourea, in the presence of acetone and water, in order to obtain the compounds of general formula (VII):

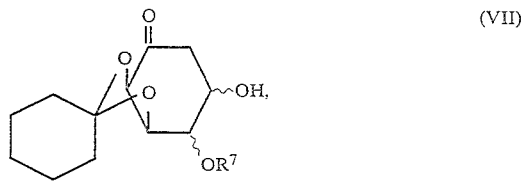

(VII)

in which

R$^7$ has the meaning given above, then, in a following stage, in selectively reducing the carbonyl functional group with cerous chloride and sodium borohydride in methanol or lithium borohydride in tetrahydrofuran in order to obtain a hydroxyl functional group which is in the axial or equatorial position on the ring depending on the reducing agent and the steric configuration of the other substituents, in then carrying out a Mitsunobu reaction which blocks the two free hydroxyl functional groups and gives them the same steric configuration, and finally in cleaving the protecting group R$^7$ in a final stage.

The process according to the invention may be illustrated by the following scheme:

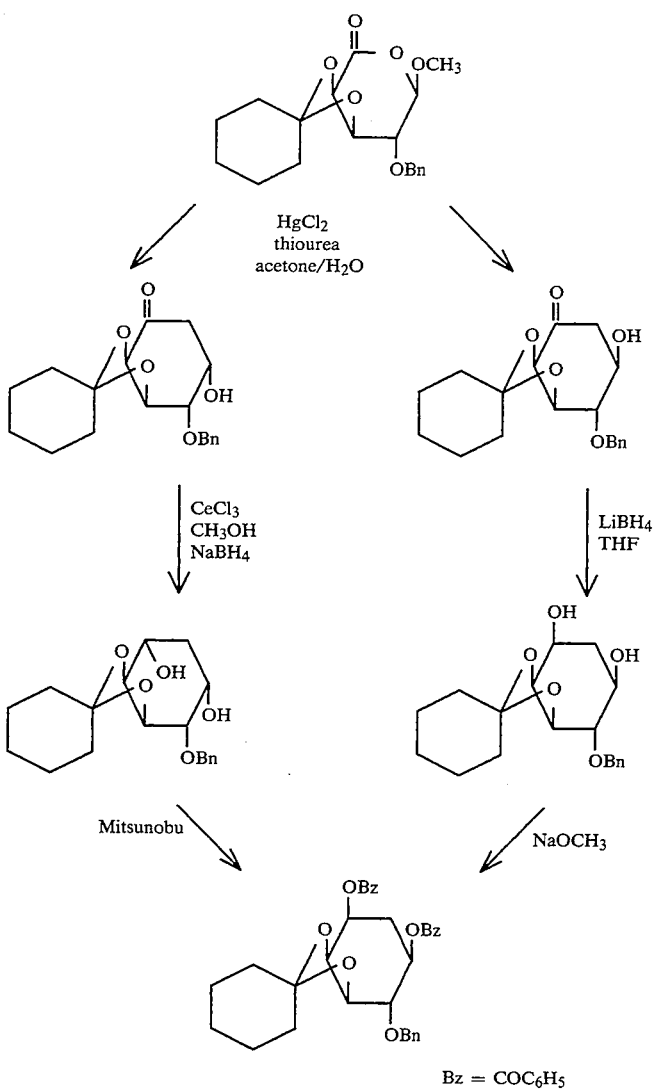

Bz = COC₆H₅

Generally, the process is implemented in a temperature range of between −10° C. and the boiling temperature of the solvent which is preferably acetone, tetrahydrofuran or methanol, and preferably in a temperature range from 0° to 100° C.

Generally, the process is implemented at normal pressure. However, it is also possible to implement the process under pressure or at reduced pressure (for example, at a pressure from $0.3 \times 10^5$ Pa to $3 \times 10^5$ Pa (0.3 to 3 bar)).

The compounds of general formula (VI) are novel and may be obtained, for example, by reacting the corresponding methyl-brominated compound with sodium hydride or caesium fluoride in dimethylformamide.

The compounds of general formula (VII) are known per se and may be prepared in the way described above.

Hydrogenolysis intended for removing the protecting groups, in particular benzyl-type protecting groups, is carried out with hydrogen in inert solvents such as alcohols, ethers or halogenated hydrocarbons or mixtures thereof, with catalysts such as Raney nickel, palladium, palladium-on-animal-charcoal or platinum. Palladium-on-animal-charcoal is preferred (see Th. Greene: "Protective Groups in Organic Synthesis", J. Wiley & Sons, 1981, New York].

The compounds according to the invention which correspond to the general formula (I) exhibit a wide spectrum of pharmacological action which was not foreseeable.

The compounds according to the invention are phospholipase C inhibitors and they moreover influence the metabolism of IP₃.

The adrenergic receptors, as well as the angiotensin II receptor, are coupled to IP₃ which acts as second messenger. Likewise, blood platelet aggregation which is induced by thrombin is influenced by the release of IP₃.

The compounds according to the invention or their salts and isomers may thus be used as active principles in medicaments. They exhibit an antiaggregation effect on thrombocytes. They may be used for the treatment of thrombo-embolic diseases and ischaemias, transient and ischaemic attacks and peripheral disorders of the blood circulation.

Moreover, they have an influence on the tonus of smooth muscles. For this reason, they can also be used in medicaments intended to influence pathologically-modified blood pressure, as coronary therapeutic agents and for the treatment of cardiac insufficiency.

Moreover, the compounds according to the invention are suitable for the treatment and the prevention of diseases of the respiratory tract, such as allergies, asthma or bronchitis, inflammations, rheumatisms, arteriosclerosis or dermatoses such as psoriasis and inflammatory dermatoses. In particular, they are suitable for the treatment and the prevention of all diseases which are accompanied by inflammatory processes.

The pharmacological effects of the substances according to the invention are determined by the following methods:

1) Competition studies with radiolabelled 1,4,5-$IP_3$ on membrane preparations arising from dog cerebellum. BBRC 146 (1987), 1071–1078 [A. J. Willcocks, A. M. Cooke, B. V. L. Potter and S. R. Nahorski, William W. Y. Lo and John Hughes, Neuroscience Letters, 81 (1987), 331–334].
2) Study of the inhibition of the dephosphorylation of 1,4,5-$IP_3$ [A.M. Cooke, S. R. Nahorski and B. L. V. Potter, FEBS-Letters, 242 (1989), 373–377].
3) Inhibition of the activation of neutrophil granulocytes (PMNL) stimulated by fMLP [see H. M. Korchak, L. E. Rutherford and G. Weissmann, I. B. C., 259 (1984), 4070–4075].

The pharmaceutical preparations which contain one or a number of compounds of general formula (I) as well as inert and nontoxic adjuvants and vehicles which are suitable from the pharmaceutical viewpoint, or which consist of one or a number of active principles of formula (I), as well as the processes for obtaining these preparations, also form part of the present invention.

In these preparations, the active principles of formula (I) must be present in a concentration from 0.1 to 99.5% by weight, preferably from 0.5 to 95% by weight, of the entire mixture.

In addition to the active principles of formula (I), the pharmaceutical preparations may contain other pharmaceutical active principles.

The pharmaceutical preparations mentioned above may be obtained in the usual way by known processes, and they may contain one or more adjuvants or vehicles.

Generally, it has appeared advantageous to administer the active principle(s) of formula (I) in total quantities from approximately 0.01 to approximately 100 mg/kg, preferably in total quantities from approximately 1 to 50 mg/kg, of body weight per 24 h, optionally in the form of a number of separate administrations, to obtain the desired result.

However, it may optionally be advantageous to depart from the quantities mentioned depending on the type of patient and on his body weight, on the individual behaviour with respect to the medicament, on the type and the seriousness of the disease, on the type of preparation and on the type of application, as well as on the time at which administration takes place or on the intervals separating the administrations.

General Instruction for the Phosphorylation and Release Process

I. Process A: Phosphoramidite Process

Preparation of a diaryl- or dialkyloxy(diisopropylamino)phosphine as phosphorylation agent

Z=diaryl or dialkyl 4.4 ml of phosphorus trichloride are added under argon to 30 ml of dry, freshly distilled ether. 14 ml of diisopropylamine in 30 ml of dry ether are added dropwise to the cooled solution at −10° C. The mixture is stirred for 1 h at −10° C. The mixture is then heated to 20° C. and filtered. At the end of 3 h, the filtrate is evaporated to dryness and is distilled. 6.3 g of dichloro(diisopropylamino)phosphine are obtained. This solid intermediate product is dissolved in 60 ml of dry acetonitrile under argon. The solution is cooled to −10° C. and 13.7 ml of diisopropylethylamine are added. To the solution which is left under argon at −10° C., 6.6 ml of corresponding distilled alcohol, dissolved in 40 ml of acetonitrile, are added dropwise. The solution is stirred for 1½ h. The temperature rises to 20° C. At the end of 12 h, the mixture is taken up in 150 ml of dichloromethane after evaporating to dryness. The organic phase is extracted by washing, first with a solution of sodium bicarbonate in water and then with water. After drying over $MgSO_4$ and evaporating to dryness, a yellow oil is obtained. 4.4 mmol of crude substance which consists largely of the title compound are thus obtained.

1. Phosphorylation a) A mixture A of x mg of alcohol to be phosphorylated and of two equivalents (per hydroxyl group to be phosphorylated) of diaryl- or dialkyloxy(diisopropylamino)phosphine is dried for ½ h under a vacuum of 6.66 Pa (0.05 mm Hg).
b) Two equivalents (with respect to the phosphinylation reactant) of tetrazole, which has been sublimed beforehand and dissolved in the minimum amount of anhydrous acetonitrile, are added under argon to the mixture A.
c) the solution is stirred under argon for 1 h at room temperature.

2. Oxidation (phosphorus III→phosphorus V)

The mixture is then diluted by addition of dichloromethane. Two equivalents (with respect to the phosphinylation reactant) of tert-butyl hydroperoxide (t-BuOOH) are then added. The solution is stirred for 3 h at room temperature under argon.

3. Separation of the phosphorylated products

An aqueous solution of sodium thiosulphate and of sodium bicarbonate is added in order to neutralise the reaction. After extracting with dichloromethane and evaporating the organic phase to dryness, separation is carried out on a plate or column of silica gel or by RP 8 or RP 18 reverse phase.

II. Process B: Pyrophosphate process

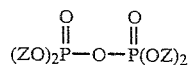

Preparation of the Phosphorylation Reactant 556 g (2 mmol) of diaryl or dialkyl hydrogen phosphate, dissolved in a mixture of 2 ml of acetonitrile and 2 ml of anhydrous ether, are added to 227 mg (1.1 mmol) of dicyclohexylcarbodiimide (DCC) dissolved in 1 ml of anhydrous ether. Acetonitrile is added until the mixture has completely dissolved. The solution is stirred. At the end of 15 min, a white precipitate is formed. After filtering the precipitate and washing with dichloromethane, the filtrate is evaporated to dryness and the residue is recrystallised front hexane (overnight at room temperature). 250 mg of solid tetrabenzyl pyrophosphate are formed. M.p.=61°–62° C.

General Phosphorylation Process x mg of alcohol are dissolved in the minimum amount of anhydrous tetrahydrofuran The solution is cooled to 0° C., 1.1 equivalents of n-butyllithium (n-BuLi) per free hydroxyl group are added and the mixture is stirred for 5 min. 1.3 equivalents of tetrabenzyl pyrophosphate per hydroxyl group to be phosphorylated are then added at −40° C. The solution is stirred for 1 h under argon. The mixture is then filtered on diatomaceous earth and eluted with ethyl acetate before being evaporated to dryness. The phosphorylated substances are isolated by separation on silica gel plates or on a Florisil or RP 8 column.

General Instruction for Releasing Derivatives of 6-deoxycyclitol Phosphate

1. Simultaneous release of the benzyl ester groups from the phosphates, and of benzyl ether and cyclohexylidene acetal groups from the cyclitols x mg of the derivative X of 6-deoxymyoinositol dibenzyl phosphate, dissolved in the minimum amount of ethanol and 1 ml of distilled water, are hydrogenated for 1 h at a pressure of 34.5×10³ Pa (5 psi) in the presence of an equivalent quantity of palladium-on-charcoal (10%). After filtering the catalyst on Whatman paper and eluting with distilled water, the organic solvent is evaporated. Part of the water is then removed. Two equivalents of tris(hydroxymethyl)aminomethane (Tris) per phosphate to be neutralised are then added. The mixture is then lyophilised.

2. Release of the benzyl ester protecting compounds on the phosphates and of the benzyl ether protecting compounds on the cyclitols without hydrolysis of the cyclohexylidene x mg of the derivative of 6-deoxymyoinositol dibenzyl phosphate, dissolved in the minimum amount of anhydrous ethanol, are hydrogenated for 1 h at a pressure of 13.8×10³ Pa (2 psi) in the presence of an equivalent quantity of palladium-on-charcoal (10%). The catalyst is removed by filtering on Whatman paper and eluting with water. Two equivalents of Tris per phosphate are added and the aqueous solution is evaporated. The mixture is then lyophilised. The analogous phosphates are obtained in the form of Tris salts. Their purity is monitored on a cellulose plate (mobile phase : isopropanol/aqueous ammonia/H₂O:5/1/4). Under these conditions, the Tris salt is replaced by aqueous ammonia and the phosphates are revealed in the form of ammonium salts.

Starting Materials

EXAMPLE 1

3,4-O-cyclohexylidene-β-D-methylgalactopyranoside

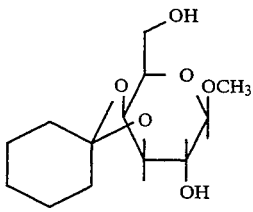

10 g (51 mmol) of β-D-methylgalactopyranoside are dissolved in 40 ml of dimethylformamide. Two equivalents of dimethoxycyclohexane (13 ml) and 0.7 ml of sulphuric acid are added and the solution is stirred for 12 h. After neutralising with sodium bicarbonate and then filtering on diatomaceous earth (elution with ethyl acetate), the title compound, which crystallises from an ethyl acetate/hexane mixture, is obtained with a yield of 90%.

M.p.=120°–121° C. $[\alpha]_D$=+82° (0.98, CH₃OH)

EXAMPLE 2

6-bromo-3,4-O-cyclohexylidene-6-deoxy-β-D-methylgalactopyranoside

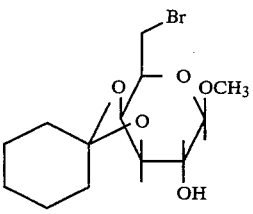

18 g (70mmol) of triphenylphosphine and 18 g (55mmol) of tetrabromomethane are added in 130 ml of anhydrous pyridine at 40° C. to a solution of 13.7 g (50mmol) of the compound of Example 1. The solution is then heated at 60° C. for 6 h. 20 ml of methanol are then added to the solution which had been cooled beforehand to room temperature. The pyridine is removed by codistillation with toluene (3×50 ml). The residue is taken up in ethyl acetate and evaporated several times in the presence of ether. The title compound is isolated by flash chromatography on silica gel: 13.5 g of product which crystallise from an ethyl acetate/hexane mixture are isolated. The yield is 80%.

M.p.=122°–123° C. $[\alpha]_D$=+21° (1.01, CH₃OH)

EXAMPLE 3

2-O-benzyl-6-bromo-3,4-O-cyclohexylidene-6-deoxy-β-D-methylgalactopyranoside

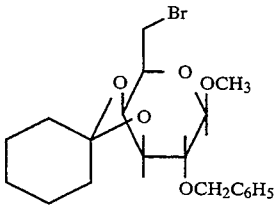

10 mg (166 mmol) of powdered potassium hydroxide (KOH) and 1 g of benzyltriethylammonium chloride (TEBAC) are added to 13.5 g (40 mmol) of the compound of Example 2, which are dissolved in 200 ml of methylene chloride. At the end of 10 min, 10 ml of benzyl bromide are added and the mixture is stirred vigorously for 12 h. 10 ml of methanol are then added to the mixture which is stirred for a further 1 h. The salts formed are removed by filtering on diatomaceous earth and the filtrate is evaporated to dryness. 13.7 g of the title compound are isolated by flash chromatography on silica gel and crystallised from hexane (yield 90%).

M.p.=94°–95° C. $[\alpha]_D = +46°$ (1, CHCl$_3$)

EXAMPLE 4

2-O-benzyl-3,4-O-cyclohexylidene-6-deoxy-$\beta$-L-arabino-hex-5-enomethylpyranoside

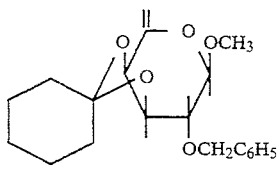

I: 1.12 g (46.8 mmol) of sodium hydride are added under argon, in three portions, to a solution of 10 g (23.4 mmol) of the compound of Example 3 in 20 ml of anhydrous dimethylformamide. The solution is stirred for 3 h and heated at 100° C. The mixture is then cooled and 10 ml of methanol are added. Stirring is continued for 1 h and then extraction with dichloromethane takes place. The organic phase is evaporated to dryness. The title compound is isolated by flash chromatography on silica gel (ethyl acetate/hexane:1/9). 7.5 g of compound are thus isolated and crystallised from n-pentane (yield 90%).

M.p.=61° C. $[\alpha]_D = -55°$ (1, CHCl$_3$)

II: 4.6 g (10.8 mmol) of the compound of Example 3 are dissolved under argon in 5 ml of anhydrous dimethylformamide. 3.3 g (21.6 mmol) of caesium fluoride (CsF), which had been dried beforehand using a vane pump, are added with 492 mg (2.16 mmol) of benzyltriethylammonium chloride (TEBAC). The solution is stirred for 4 h at 120° C. The mixture is then cooled to room temperature and extracted with dichloromethane. The organic phase is evaporated to dryness and then 3.2 g of the title compound are isolated by crystallising from n-pentane (yield 85%).

M.p.=61°–62° C. $[\alpha]_D = -55°$ (1, CHCl$_3$)

EXAMPLES 5 AND 6

2-D-(2,3/4,5)-4-O-benzyl-2,3-O-cyclohexylidene-1-oxo-2,3,4,5-cyclohexanetetrol

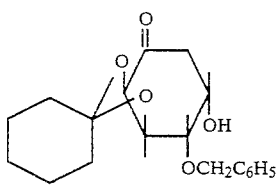
(Example 5)

2-D-(2,3,5/4)-4-O-benzyl-2,3-O-cyclohexylidene-1-oxo-2,3,4,5-cyclohexanetetrol

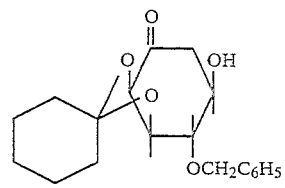
(Example 6)

1.7 equivalents (2.45 mmol, 665 mg) of mercuric chloride (HgCl$_2$) are added to 500 mg of the compound of Example 4 (1.44 mmol) dissolved in 18 ml of an acetone/water (2/1) mixture. The solution is stirred for 20 min and then 4 eq/HgCl$_2$ of thiourea (745 mg) are added. Stirring is continued for 2 h. After filtering on diatomaceous earth, washing the precipitate with acetone and evaporating the organic solvent, the residue is extracted with ethyl acetate. The organic phase is evaporated to dryness and 400 mg of a mixture of the two ketones 5 and 6 are recovered. The total yield of the reaction is 95%. By separating by flash chromatography on silica gel (elution: AcOEt/hexane: 2/8), it is possible to isolate the two 6-deoxyinososes 5 and 6. The total yield after separating is greater than 85%. The ratio of the 5 and 6 isomers is 1/1. Isomer 5, which is eluted first, is in the form of a syrup, $[\alpha]_D = +10°$ (C=10.3, CHCl$_3$). Isomer 6 is crystallised from n-pentane.

M.p.=79°–80° C. $[\alpha]_D = -6°$ (1, CHCl$_3$)

EXAMPLES 7 AND 8

4-O-benzyl-2,3-O-cyclohexylidene-6-deoxy-D-myoinositol

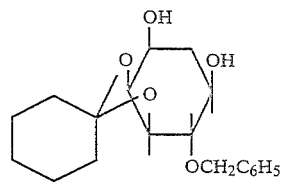
(Example 7)

3-O-benzyl-1,2-O-cyclohexylidene-5-deoxy-D-chiroinositol

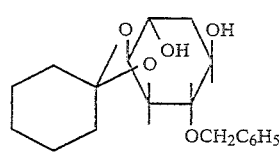
(Example 8)

1 g (3 mmol) of the compound of Example 6 is dissolved in 20 ml of anhydrous tetrahydrofuran. 142 mg of lithium borohydrate (LiBH$_4$) are added to the solution which is stirred for 1 h at −78° C. under argon. 5 ml of a saturated aqueous sodium chloride solution are then added and the temperature of the reaction is brought to 20° C. The mixture is stirred for 12 h at 20° C. After evaporating to dryness, the residue is diluted several times in 30 ml of isopropanol and then evaporated to dryness. The mixture is then taken up in ethyl acetate and filtered on diatomaceous earth. The filtrate is concentrated and the title compound of Example 7 is isolated by crystallising from an ethyl acetate/n-pentane mixture. There appears 868 mg (2.6 mmol) with a yield greater than 85%.

M.p.=124°-125° C. [α]_D= -5° (0.9, CHCl_3)

The compound of Example 8 is obtained by isolating from the mother liquor with a yield of 10%. [α]_D= +20° (c=1.1, CHCl_3)

EXAMPLE 9

5,6-O-cyclohexylidene-3-deoxy-L-chiroinositol

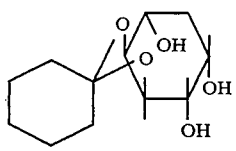

350 mg (1.05 mmol) of 1-O-benzyl-5,6-O-cyclohexylidene-3-deoxy-L-chiroinositol in 20 ml of ethyl acetate are hydrogenated for 1 h at a pressure of $20.7 \times 10^3$ Pa (3 psi) in the presence of 350 mg of palladium-on-charcoal (10%). The catalyst is removed by filtering on Whatman paper and eluting with ethanol. The filtrate is evaporated to dryness and the title compound is crystallised from chloroform. 250 mg (1.02 mmol) of compound are isolated with a yield of 97%.

M.p.=136°-137° C. [α]_D= -38° (c=0.8, CH_3OH)

EXAMPLE 10

2,3-O-cyclohexylidene-6-deoxy-D-myoinositol

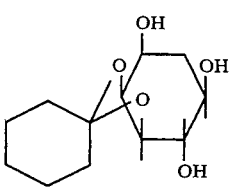

110 mg (0.33 mmol) of 4-O-benzyl-2,3-O-cyclohexylidene-6-deoxymyoinositol (Example 7) in a solution of 10 ml of ethyl acetate are hydrogenated for 2 h at a pressure of $34.5 \times 10^3$ Pa (5 psi) in the presence of 55 mg of palladium hydroxide on charcoal (20%) and of 10 mg of calcium carbonate. The catalyst is removed by filtering on Whatman paper (elution with ethanol), and the filtrate is evaporated to dryness. 77 mg (0.31 mmol) of the title compound are recrystallised from chloroform (yield 95%).

M.p.=134°-135° C. [α]_D= +42° (1.3, CH_3OH)

EXAMPLE 11

2,3-O-cyclohexylidene-6-deoxy-D-myoinositol 1,4,5-tris(dibutyl phosphate)

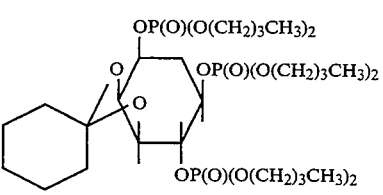

The compound of Example 10 is phosphorylated with 6 equivalents of dibutyl (diisopropylamino) phosphine by Phosphoramidite Process [A]. After flash chromatography, the title compound is obtained with a yield of 55%. [α]_D= +3.8° (c=3, CHCl_3)

PREPARATION EXAMPLES

EXAMPLE I 6-deoxy-D-myoinositol 3,4,5-tris(dibutyl phosphate)

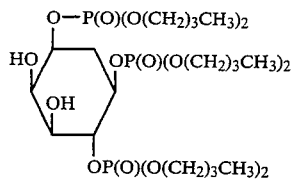

200 mg of 2,3-O-cyclohexylidene-6-deoxy-D-myoinositol 1,4,5-tris(dibutyl phosphate) are stirred with 2 ml of 2N hydrochloric acid in methanol for 2 h at room temperature. The solution is completely concentrated under vacuum. After flash chromatography on silica gel (solvent ethyl acetate), the title compound is obtained with a yield of 144 mg (80% of theory). [α]_D= 17° (c=1.1, CHCl_3)

EXAMPLE II 2,3-di-O-myristoyl-6-deoxy-D-myoinositol 1,4,5-tris(dibutyl phosphate)

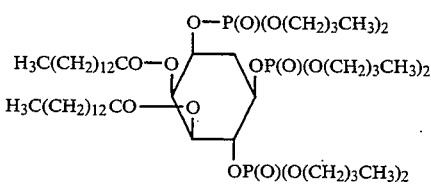

74 mg (0.1 mmol) of the compound of Example I are dissolved in 10 ml of dichloromethane, and then 54 mg (0.26 mmol) of dicyclohexylcarbodiimide, 59 mg (0.26 mmol) of myristic acid and 20 mg of dimethylaminopyridine are added at room temperature. The solution is heated for 4 h, filtered on diatomaceous earth (CH_2Cl_2) and concentrated to dryness under vacuum. After flash chromatography on silica gel (solvent: ethyl acetate/heptane 1/1), the title compound is obtained with a yield of 80%.

M.p.=37°-38° C. [α]_D= +7.8° (c=1.8, CHCl_3)

Example III 2,3-di-O-palmitoyl-6-deoxy-D-myoinositol 1,4,5-tris(dibutyl phosphate)

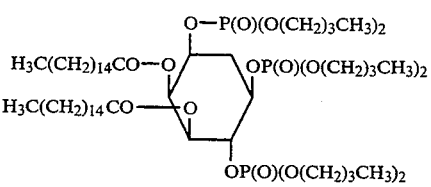

The title compound is obtained by following the instructions of Example II.

[α]_D= +7.8° (c=1.8, CHCl_3) M.p.=37°-39° C.

We claim:

1. Substituted derivatives of deoxymyoinositol, characterised in that they correspond to the general formula (I):

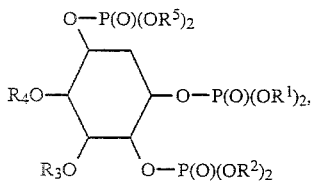

(I)

in which
R[1], R[2] and R[5] are identical or different and represent a linear or branched alkyl group of 3 to 14 carbon atoms,
R[3] and R[4] are identical or different and represent a hydrogen atom, a protecting group of the hydroxyl groups or the residue of formula —CO—(CH$_2$)$_n$—CH$_3$
in which
n represents the number 12, 13, 14, 15, 16 or 17, and their salts.

2. Derivatives according to claim 1, characterised in that
R[1], R[2] and R[5] are identical or different and represent a linear or branched alkyl group of 4 to 8 carbon atoms,
R[3] and R[4] are identical or different and represent a hydrogen atom, a benzyl group or the residue of formula —CO—(CH$_2$)$_n$—CH$_3$
in which
n represents the number 12, 13, 14, 15 or 16, and their salts.

3. Derivatives according to claim 1, characterised in that
R[1], R[2] and R[5] are identical or different and represent a linear or branched alkyl group of 4 carbon atoms,
R[3] and R[4] are identical or different and represent a hydrogen atom or the residue of formula —CO—(CH$_2$)$_n$—CH$_3$ in which
n represents the number 12, 13, 14 or 15, and their salts.

4. Derivatives according to claim 1, characterised in that
R[1], R[2] and R[5] represent the n-butyl group, and
R[3] and R[4] are identical or different and represent a hydroxyl atom or the residue of formula —CO—(CH$_2$)$_n$—CH$_3$ in which
n represents the number 12 or 14, and their salts.

5. A compound according to claim 1 wherein such compound is 6-deoxy-D-myoinositol 3,4,5-tris(dibutyl phosphate) of the formula

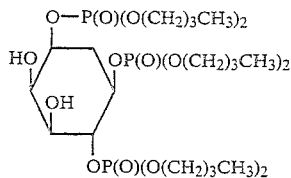

and salts thereof.

6. A compound according to claim 1 wherein such compound is 2,3-di-O-myristoyl-6-deoxy-D-myoinositol 1,4,5-tris(dibutyl phosphate) of the formula

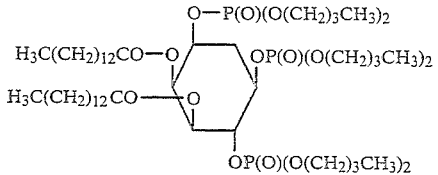

and salts thereof.

7. A compound according to claim 1 wherein such compound is 2,3-di-O-palmitoyl-6-deoxy-D-myoinositol 1,4,5-tris(dibutyl phosphate of the formula

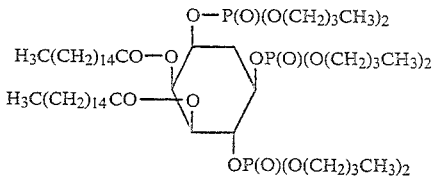

and salts thereof.

8. A composition for the treatment of inflammation comprising an amount effective therefor of a compound or salt thereof according to claim 1 mad a pharmacologically acceptable diluent.

9. A method of treating inflammation in a patient in need thereof which comprises administering to such patient an amount effective therefor of a compound or salt thereof according to claim 1.

* * * * *

UNITED STATES PATENT AND TRADEMARK OFFICE
CERTIFICATE OF CORRECTION

PATENT NO. : 5,407,923
DATED      : April 18, 1995
INVENTOR(S): Bischoff, et al.

It is certified that error appears in the above-indentified patent and that said Letters Patent is hereby corrected as shown below:

Col. 17, line 47    Delete " hydroxyl " and substitute -- hydrogen --

Col. 18, line 43    Delete " mad " and substitute -- and --

Signed and Sealed this

Eighth Day of August, 1995

Attest:

BRUCE LEHMAN

*Attesting Officer*    *Commissioner of Patents and Trademarks*